(12) United States Patent
Granite et al.

(10) Patent No.: US 8,069,703 B1
(45) Date of Patent: Dec. 6, 2011

(54) SEMI-CONTINUOUS DETECTION OF MERCURY IN GASES

(75) Inventors: Evan J. Granite, Wexford, PA (US); Henry W. Pennline, Bethel Park, PA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 1040 days.

(21) Appl. No.: 11/947,815

(22) Filed: Nov. 30, 2007

(51) Int. Cl.
  *G01N 29/02* (2006.01)
(52) U.S. Cl. ...................................... 73/24.01
(58) Field of Classification Search .............. 73/24.01, 73/64.53
  See application file for complete search history.

(56) References Cited

U.S. PATENT DOCUMENTS

| | | | |
|---|---|---|---|
| 5,112,642 A * | 5/1992 | Wajid ............................... | 427/10 |
| 5,879,948 A * | 3/1999 | Van Pelt et al. ................. | 436/81 |
| 6,521,021 B1 * | 2/2003 | Pennline et al. ................. | 95/134 |
| 6,576,092 B2 * | 6/2003 | Granite et al. ............. | 204/158.2 |
| 6,699,440 B1 * | 3/2004 | Vermeulen ..................... | 422/177 |
| 7,454,945 B1 * | 11/2008 | Kita et al. ...................... | 73/1.03 |
| 7,454,952 B2 * | 11/2008 | Kita et al. ..................... | 73/31.03 |
| 7,500,379 B2 * | 3/2009 | Hines ........................... | 73/24.06 |
| 7,562,556 B2 * | 7/2009 | Johnston et al. ............. | 73/23.31 |
| 2009/0107217 A1 * | 4/2009 | Huang .......................... | 73/61.42 |

FOREIGN PATENT DOCUMENTS

JP        2008286656 A    * 11/2008

* cited by examiner

*Primary Examiner* — John Fitzgerald
(74) *Attorney, Agent, or Firm* — James B. Potts; Brian J. Lally; John T. Lucas

(57) ABSTRACT

A new method for the semi-continuous detection of heavy metals and metalloids including mercury in gaseous streams. The method entails mass measurement of heavy metal oxides and metalloid oxides with a surface acoustic wave (SAW) sensor having an uncoated substrate. An array of surface acoustic wave (SAW) sensors can be used where each sensor is for the semi-continuous emission monitoring of a particular heavy metal or metalloid.

21 Claims, 3 Drawing Sheets

Figure 2: Array of Photodeposition Detectors for Determination of Metals in a Gas Stream
a) Sequential Array in Series
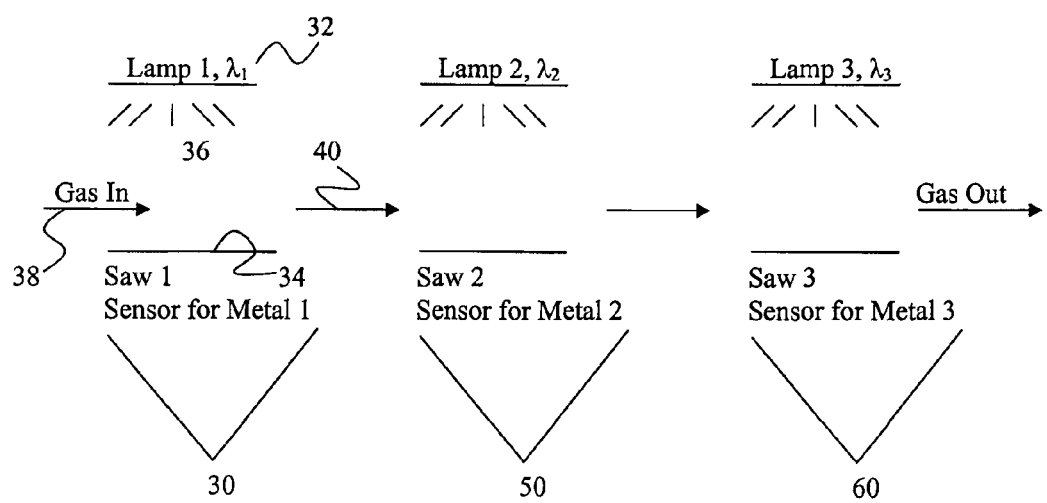

Figure 3: Array of Photodeposition Detectors for Determination of Metals in a Gas Stream
b)  Array in Parallel
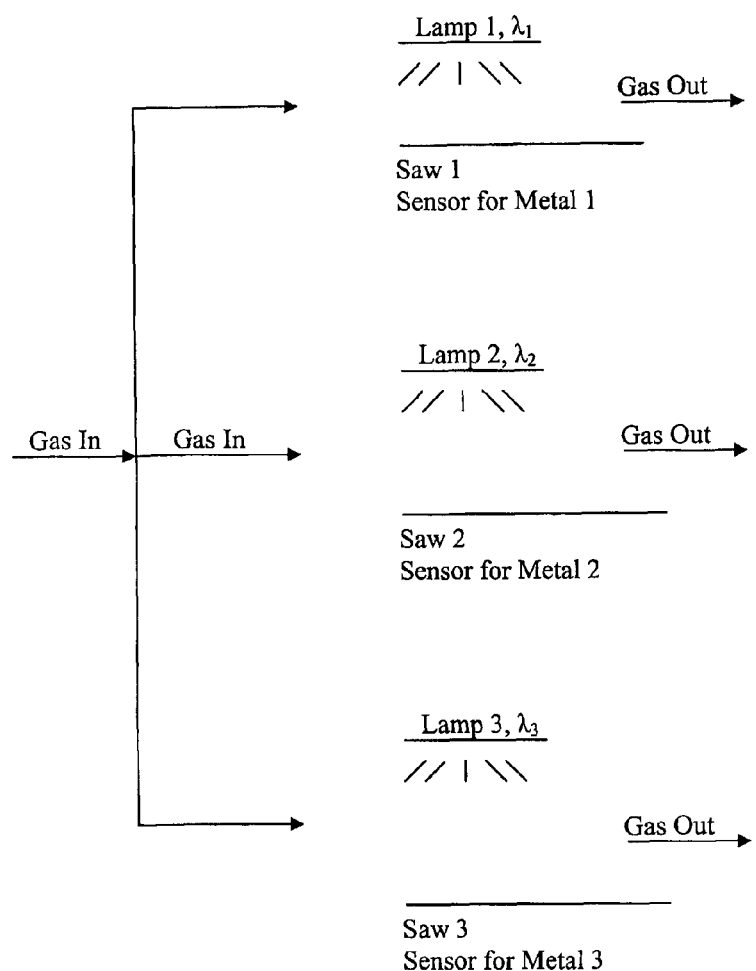

SEMI-CONTINUOUS DETECTION OF MERCURY IN GASES

The United States Government has rights in this invention pursuant to the employer-employee relationship of the Government to the inventors as U.S. Department of Energy employees at the National Energy Technology Laboratory.

BACKGROUND OF THE INVENTION

1. Field of the Invention

This invention relates to the quantitative detection of heavy metals and metalloids in effluent gases, and more specifically, this invention relates to a method for the quantitative detection of heavy metals such as mercury (Hg) in high temperature gases generated from sources such as coal gasifiers, coal-fired electrical generating plants, ore smelters, and waste incinerators.

2. Background of the Invention

Coal-burning power plants, incinerators, oil-burning boilers and power plants, refuse-derived fuel power plants, and gasification systems are sources of effluent streams with mercury and other heavy metals. These metals are toxic. The combustion of low-rank coals such as Powder River Basin sub-bituminous coal and lignites have been shown to form flue gases where the mercury is primarily in the elemental form. In the gasification of coal, mercury is primarily in the elemental form.

Elemental mercury is difficult to capture from a gas stream. For example, elemental mercury is a semi-noble metal, insoluble in water, and is not efficiently captured by carbon. Much of the mercury contained in power plant flue gas is in the elemental form.

In 2005 the U.S. Environmental Agency (EPA) announced the Clean Air Mercury Rule (CAMR) which places permanent limits on mercury emissions from coal-fired utility boilers and establishes a mercury cap-and-trade program. CAMR will be implemented in two phases, with a first phase annual limit of 38 tons in 2010 followed by a final annual limit of 15 tons to be in effect in 2018. The final limit requires an approximately 70% reduction from 1999 emission levels.

The EPA prefers continuous emission monitoring (CEM) for mercury. CEM monitors for mercury often utilize methods to oxidize all of the mercury present within a slipstream of flue gas in order to facilitate the capture and detection of the mercury. Coal-burning power plants have an electrical power capability of 300 GigaWatts (GW) and constitute a potential market of approximately $100,000,000 for CEM. Other markets include incinerators, natural gas pipelines, gasification systems, chemical process plants, and research and health/safety (air monitoring).

Many technologies are being developed for the control of mercury emissions from flue gases. These methods employ sorbents, catalysts, scrubbing liquors, flue gas or coal additives, combustion modification, barrier discharges, and ultraviolet (UV) radiation for the removal of mercury. These removal methods need support in the form of reliable and inexpensive CEM.

There are commercial devices currently available which offer CEM. These devices often include a gold or sorbent trap with subsequent determination of Hg concentration via UV spectrophotometry. Other methods that involve pretreatment of the stream to be analyzed include real time atomic absorption and X-ray fluorescence. See D. S. Zanzow, S. J. Bajic, D. E. Eckels, and D. P. Baldwin, "Real-Time Atomic Absorption Mercury Continuous Emission Monitor," *Review of Scientific Instruments*, 74 (8):3774-3783 (2003); K. J. Hay, B. E. Johnson, P. R. Ginochio, and J. A. Cooper, "Relative Accuracy Testing of An X-Ray Fluorescence-Based Mercury Monitor at Coal-Fired Boilers," *J. Air & Waste Manage. Assoc.* 56 (May):657-665 (2006); and S. Kellie, Y. Duan, Y. Cao, P. Chu, A. Mehta, R. Carty, K. Liu, W. P. Pan, and J. T. Riley, "Mercury Emissions From a 100-MW Wall-Fired Boiler as Measured by Semicontinuous mercury Monitor and Ontario Hydro Method," *Fuel Processing Technology*, 85 487-499 (2004).

The aforementioned methods are often labor intensive, can be slow, and are often costly. In addition, the methods are often prone to numerous interferences. For example, ozone ($O_3$), which may be found in effluent gas streams, absorbs UV, therefore interfering with those processes using UV light to measure and to transform elemental mercury into ions. This phenomenon is described in Y. Li, S. R. Lee, and C. Y. Wu, "UV-Absorption-Based Measurements of Ozone and Mercury: An Investigation on Their Mutual Interferences," *Aerosol and Air Quality Research*, 6 (4), 418-429 (2006). Other quenching agents such as $O_2$, HCl, $H_2O$, $CO_2$, $SO_x$, and $NO_x$ also must be removed before UV measurements can be carried out.

Surface acoustic wave (SAW) sensors with a gold-coated substrate are used to develop a continuous emission monitoring system for mercury. This is described in "Semi-Annual Technical Progress Report: Surface Acoustic Wave Mercury Vapor Sensor," Document Number: DE-AR26-97FT34316-002.12 (Jun. 2, 1998), submitted by Sensor Research and Development Corporation, Orono, Maine to U.S. DOE, Morgantown Energy Technology Center, Morgantown, W. Va. However, the gold on gold-coated substrates in SAW sensors can dissolve moieties other than mercury and become contaminated and thus give inaccurate results. The same problem exists with gold used as a trap supra for mercury. Gold is attacked by aqua regia ($HCl+HNO_3$) and hot sulfuric acid ($H_2SO_4$), and reacts with ozone to form gold oxide.

Removal of elemental mercury from effluent gas streams via irradiation with UV light is described in C. R. McLamon, E. J. Granite, and H. W. Pennline, "The PCO Process For Photochemical Removal of Mercury From Flue Gas," Fuel Processing Technology, 87 85-89 (2005); E. J. Granite and H. W. Pennline, "Photochemical Removal of Mercury From Flue Gas," Ind. Eng. Chem. Res., 41 5470-5476 (2002); E. J. Granite, H. W. Pennline, and J. S. Hoffman, Effects of Photochemical Formation of Mercuric Oxide, Ind. Eng. Chem. Res., 38 5034-5037 (1999); and in U.S. Pat. No. 6,576,092 awarded to Granite et al., on Jun. 10, 2003. The aforementioned McLamon et al. article and the Granite et al. patent are incorporated herein by reference.

U.S. Pat. No. 7,033,419 awarded to Granite, et al. on Apr. 25, 2006 discloses a process to facilitate mercury extraction from high temperature flue/fuel gas via the use of metal sorbents which capture mercury at high and ambient temperatures.

U.S. Pat. No. 6,690,462 awarded to Seltzer on Feb. 10, 2004 discloses a process, system and apparatus to calibrate a continuous emission mercury monitoring system based on plasma emission spectrometry.

U.S. Pat. No. 6,521,021 awarded to Pennline, et al. on Feb. 18, 2003 discloses a process to facilitate mercury extraction from high temperature flue/fuel gas by adsorption onto a thermally activated sorbent produced in situ at the power plant.

U.S. Pat. No. 5,679,957 awarded to Durham, et al. on Oct. 21, 1997 discloses a process to monitor mercury emissions by UV spectrophotometry.

U.S. Pat. No. 4,713,547 awarded to Grossman on Dec. 15, 1987 discloses a process to monitor mercury emissions by UV spectrophotometry.

None of the aforementioned articles or patents discloses an inexpensive and reliable method for semi-continuous monitoring of pollutants in effluent gas streams.

None of the aforementioned articles or patents discloses a method for semi-continuous monitoring of mercury and other heavy metals and metalloids which is free from interferences from moieties such as aqua regia ($HCl+HNO_3$) and, independently, ozone.

A need exists in the art for a reliable and interference-free semi-continuous detection method for mercury and other heavy metals and metalloids in effluent gas streams.

SUMMARY OF THE INVENTION

It is an object of the present invention to provide a semi-continuous heavy metal and metalloid detection method for effluent gas streams that overcomes many of the disadvantages of the prior art.

Another object of the present invention is to provide a method for continuous detection and measurement of toxic metals in gaseous, liquid or solid streams. A feature of the invention is that heavy metals and metalloids are deposited as oxides on surface acoustic wave sensors and substrates positioned in close spatial relationship to the sensors. An advantage of the invention is that it provides substantially immediate determination of concentrations of the toxic metals in the streams.

Still another object of the present invention is to provide a photo-deposition method for detecting and measuring toxic metals in liquid and solid phases. A feature of this invention is that the target metal (e.g., mercury) is liberated from the solution via a reducing agent and swept into an oxygen stream to be irradiated into an oxide. Another feature of the invention is the in situ provision for the oxide to condense upon a quartz sensing element to provide nearly instant mass measurement of the oxide. An advantage of the invention is the elimination of the need for scrubbing solutions.

Yet another object of the present invention is to provide a method for detecting and measuring toxic metals in effluent which is free of interferences from other moieties present in the effluent gas stream. A feature of this invention is that other moieties which cause interference in other methods serve as a means to ensure complete deposition of the heavy metal/metalloid oxide. An advantage of this feature is greater detection levels, leading to greater accuracy.

Still another object of the present invention is to provide a method where many heavy metals and metalloids can be simultaneously detected in an effluent gas. A feature of this invention is that an array of surface wave sensors are used. An advantage of this feature is that each sensor is dedicated to the detection of a particular metal oxide or metalloid oxide. Another advantage is that the use of an array gives rise to a greater range of heavy metal and metalloid determination.

Yet another object of the present invention is to provide a heavy metal/metalloid detection method with low energy consumption. A feature of this invention is that only a small slipstream of effluent gas is used for the detection of each heavy metal or metalloid. Another feature is that much of the energy for this invention is derived from the effluent gas itself. An advantage of these features is low energy usage and even lower costs.

Still another object of the present invention is to provide a dry system for continuous emission monitoring of heavy metals and metalloids in effluent gas streams. A feature of this invention is the photodeposition of oxides of the metals and metalloids upon a piezoelectric oscillator element in a surface acoustic wave mass sensor. An advantage of the invention is the substantially immediate determination of concentration of the heavy metals and metalloids in the sample stream. Another advantage that there is nothing to replenish and no liquids to remove and/or reclaim from the system.

Briefly, the invention provides a method for the semi-continuous detection of heavy metals and metalloids in effluent gas streams by mass measurement of heavy metal oxides and metalloid oxides with a surface acoustic wave (SAW) sensor having an uncoated substrate.

Specifically, the invention provides a method for the semi-continuous detection of heavy metals and metalloids in effluent streams, the method comprising contacting the effluent to an oxidizing fluid; subjecting the effluent to radiation to oxidize the metals and metalloids; depositing the oxidized metals and metalloids onto a piezoelectric oscillator having a first oscillating frequency; and determining a second oscillating frequency of the oscillator. The change in the "weight" of the sensor surface (due to the deposition of the oxidized mercury) is manifested by a change in the oscillation frequency.

In addition, the invention provides a device comprising an array of surface acoustic wave (SAW) sensors with each sensor tailored to detect a particular metal oxide or metalloid oxide.

DESCRIPTION OF THE DRAWING

These and other objects and advantages of the present invention will become readily apparent upon consideration of the following detailed description and attached drawing, wherein:

FIG. 2 is a schematic diagram of the SAW sensors arranged in series, in accordance with features of the present invention; and FIG. 3 is a schematic diagram of SAW sensors arranged in parallel, in accordance with features of the present invention.

DESCRIPTION OF INVENTION

Figure 1:
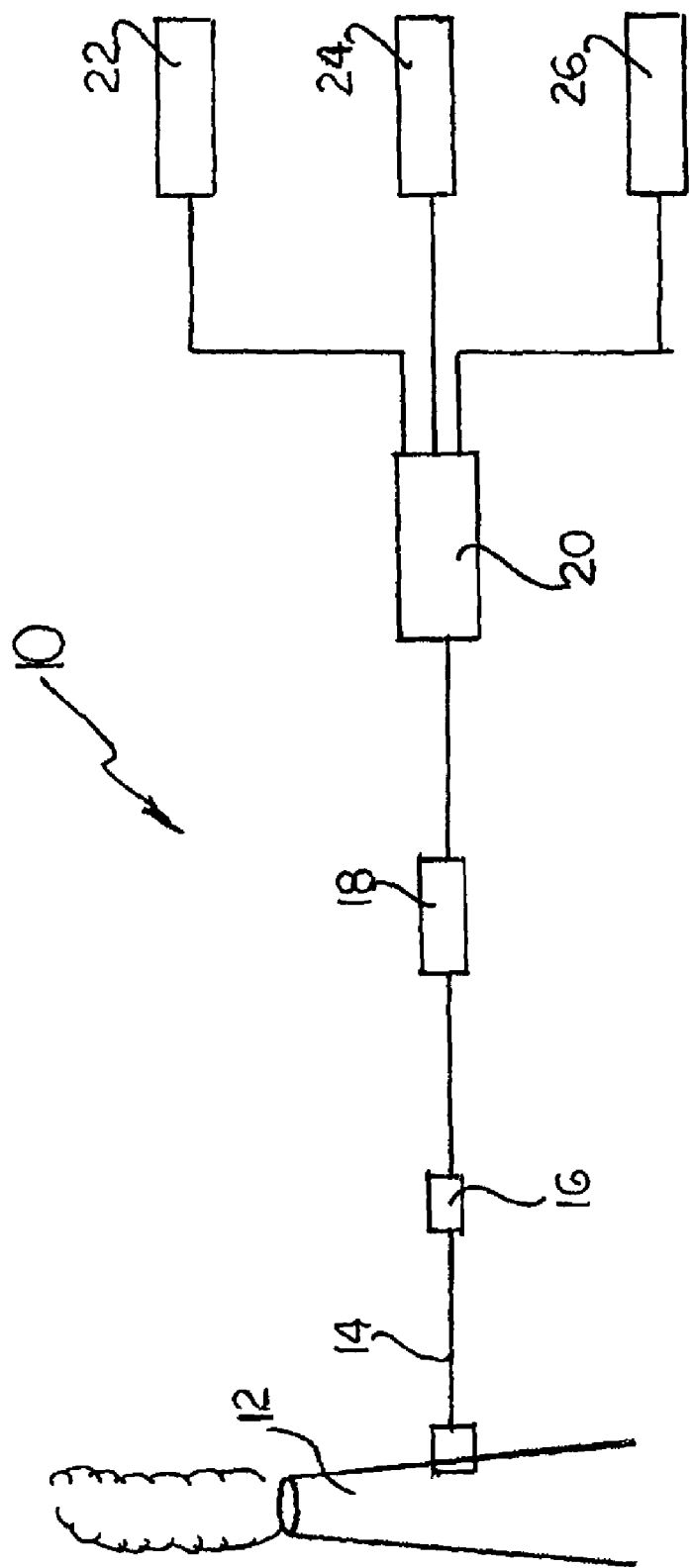
FIG. 1: is a schematic depiction of the invented detection process, in accordance with features of the present invention.

The inventors have devised a new photo-deposition method for the semi-continuous detection of heavy metals and metalloids in gaseous streams. The method measures how the mass of the oxidized moieties of metals and metalloids deposited on a piezoelectric oscillator changes the oscillation frequency of the oscillator. Thus, the method includes mass determination, and thus complete quantitative determination for such media as flue gases, syngas, natural gas, chemical process gases, and air. Liquid and solid phase analysis is also provided.

In one embodiment of the invention, total mercury is measured on a continuous basis. Detection of mercury is facilitated via photodeposition of mercuric oxide using 254 nanometer wavelength light. The formation of mercuric oxide is enhanced by blending in air or oxygen to a slipstream of flue gas prior to irradiation. Upon irradiation, mercuric oxide is photodeposited with near 100 percent efficiency on a SAW mass sensor. Inasmuch as mercuric oxide will readily condense on surfaces, the SAW sensor does not need a gold film. This no gold-containing deposition surface is a major advantage given known poisoning issues associated with gold and flue gas constituents, and is applicable for other target metals.

The invention determines mass of target moieties using surface acoustic wave (SAW) sensors, whereby the sensors comprise uncoated substrates such as quartz. The substrates which are contacted by a heavy metal oxide or a metalloid oxide, result in deposition of said oxide upon the substrate.

Another salient feature is the use of an array of SAW (piezoelectric) sensors, each sensor specific for a particular heavy metal oxide or metalloid oxide.

This invention does not require a coating for the SAW substrate. (This contrasts with gold-coated substrates, which present obvious cost factors, but also is responsible for toxic emissions of their own.) Rather the substrate is selected from the group consisting of quartz, lithium tantalate ($LiTaO_3$), lithium niobate ($LiNbO_3$), and combinations thereof. The method is applicable for detecting a myriad of metals, including, but not limited to, mercury (Hg), cadmium (Cd), and zinc (Zn). Target metalloids include, but are not limited to, arsenic (As) and selenium (Se).

The use of SAW mass sensors comprised of uncoated quartz substrates is the preferred embodiment for heavy metal and metalloid detection in the instant invention. In this preferred embodiment, the quartz is utilized such that the target moieties contact the quartz directly with no film, catalytic surface, or other substrate overlaying the quartz.

Other detection methods include, but are not limited to, a gold trap for the heavy metal with subsequent analysis via conductivity, colorimetry, UV spectrometry (AAS, AFS, ICP) and/or mass spectrometry.

Any heavy metals initially present in the gaseous streams in oxidized form are reduced to the elemental metal, e.g., $Hg^{2+} \rightarrow Hg^0$, by heating in excess of 510° C. (950° F.). The effluent gas stream is contacted with an oxidizing gas. The preferred gas is oxygen ($O_2$).

FIG. 1 is a schematic diagram of the method, designated in numeral 10. The effluent gas stream for the purposes of this invention can be just a "slipstream," 14 such as a small portion of the main effluent stream 12 diverted for emission monitoring purposes. The slip stream 14 is preheated in a furnace or other heating means 16 such as a thermal cracker, and then subjected to an oxidizing source, 18, such as oxygen, air, or other oxygen containing fluids. Typical preheating temperatures are above 500° C. Prior to being subjected to an oxidizing source, the effluent is quenched.

The mixture is then irradiated with ultra violet radiation to facilitate photolysis of oxygen and subsequent formation of ozone. The ozone reacts with elemental mercury to form mercuric oxide.

After treatment in a UV exposure step 20, the slip stream contacts a SAW sensor. A single SAW sensor or a plurality of sensors 22, 24, 26 can be provided for each element (e.g. Hg, Cd, Se) subjected to CEM. Temperatures ($T_1$) of this deposition process range from 80° F.$\leq T_1 \leq$280° F.

Whereas FIG. 1 employs just one radiation source 20 to facilitate photochemical production of deposition moieties, a plurality of radiation emitters can be employed in the invented method.

As depicted in FIGS. 2 and 3, a plurality of photochemical modules, each module specific for one of a plurality of target metals, is provided. FIG. 2 shows the invented system whereby SAW sensors are placed in series relative to each other such that downstream situated modules treat effluent after the effluent has contacted upstream modules. A first module 30 as depicted in FIG. 2 comprises a radiation source 32 specific to one wave length ($\lambda_1$) or radiation type, and a surface acoustic wave sensor 34, adapted to receive deposition of a predetermined deposition moiety or first target metal. The sensor 34 is positioned in opposition to the radiation source and spaced in close spatial relation thereto to ensure contact of all converted moieties to surfaces of the sensor prior to exit of the converted moieties from the module. In one embodiment, the sensor is positioned inferior to the radiation source so as to utilize gravity in facilitating deposition of converted metal moiety onto a surface of the sensor.

A passageway 36 situated intermediate the radiation source 32 and the sensor 34 is adapted to transport fluid through the module. An upstream region of the passageway defines a means of ingress 38 for the fluid. Similarly, a downstream region of the passageway defines a means of egress 40 for fluid to exit the module 30 after a time considered sufficient to photochemically treat the fluid to effectuate nearly complete conversion of the first target metal and deposition of the converted metal onto the sensor 34.

Once substantially all of the first target metal is photoconverted, or otherwise deposited on the surface of the first sensor 34, the targets remaining in the residual effluent are subjected to subsequent treatment by additional modules 50 and 60, which are placed in series to the first module 30. Each of these modules feature different radiations ($\lambda_{1+n}$) wherein n is an integer to denote a different type of radiation (infra red, gamma, alpha, beta radiation) than ultra violet, or alternatively, n denotes a different wavelength value within the same spectrum (e.g., ultra violet spectrum).

FIG. 3 shows an embodiment of the invented system whereby photochemical conversion of different target moieties in a single effluent stream occurs simultaneously. FIG. 3 depicts treatment modules arranged in a parallel array instead of in series. This arrangement allows operators to take a module off line when the main effluent does not contain moieties normally treated by that module. Individual module construction is similar to that depicted in FIG. 2.

The following illustrations utilize specific UV radiation values. However, a myriad of UV energies are suitable for use in the method, including those selected from the range of 180 nanometers (nm) to 254 nm. Application of UV light (having a wavelength of less than 240 nm) to an oxygen-containing stream will result in the formation of ozone. This is useful in the determination of arsenic and selenium via oxidation by the ozone formed. Longer UV wavelengths, such as 253.7 nm, provide means for the specific determination of mercury.

In one embodiment of the invention, a particulate-free slipstream of flue gas is heated to temperatures above 950 F, converting all of the mercury to its elemental form. A small stream of oxygen or air is blended into the slipstream, which is cooled to temperatures below 280 F. Shortwave (254 nm or shorter) ultraviolet light is applied to the resulting gas mixture, yielding quantitative deposition of mercuric oxide upon a quartz substrate. The quartz substrate is a piezoelectric oscillator element in a surface wave acoustic mass sensor. The mass of mercuric oxide deposited upon the quartz substrate results in a change in the frequency of the oscillator, resulting in detection of mercury. The quartz substrate is cleaned of the oxide, either by heating or with an aqua regia rinse. An advantage of this embodiment is that the need for scrubbing solutions is eliminated.

In another embodiment of the invention, mercury present in flue gas is captured in scrubber liquids. Different scrubber liquids are used to distinguish between elemental and oxidized forms of mercury. A reducing agent is used to liberate the mercury into an oxygen stream. Short wave ultraviolet radiation is applied to the resulting mercury-oxygen mixture so as to form mercuric oxide. The oxide condenses upon a quartz substrate as discussed supra.

The reducing agent-oxygen sweep-irradiator-SAW combination outlined supra also can be used to detect target metals in liquids and solids. In this case, scrubbing solution is not needed. The liquid or solid is digested in an acid solution. Toxic metal, such as mercury, is liberated from the solution by a reducing agent and swept into an oxygen stream. UV radiation is applied to the mercury-oxygen stream, and the resulting mercuric oxide condenses upon the quartz sensing element.

Elemental mercury metal atoms are oxidized in the presence of oxidizing agents and UV light with the wavelength of 253.7 nanometers (nm) according to Equation 1.

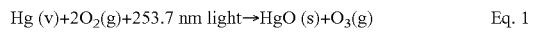

Eq. 1

The chemistry of deposition and removal depicted in Equation 1 is similar for other heavy metals and metalloids to be monitored. Specifically, UV wavelengths shorter than 253.7 nm can be used for the conversion of other heavy metals and metalloids to their respective oxides. The shorter UV wavelengths convert oxygen to ozone ($O_3$) which oxidizes the other heavy metals and metalloids.

Another approach uses UV to directly ionize the heavy metal/metalloid to, form heavy metal oxide/metalloid oxide. Table 1 infra gives the first ionization energies of a number of heavy metals and metalloids in both electron volts (eV) and the UV wavelength in nm which has that same energy necessary for the first ionization.

TABLE 1

First ionization energies and corresponding UV wavelengths for selected heavy metals and metalloids

| Element | First Ionization Energy (eV) | Wavelength (nm) |
|---|---|---|
| As | 9.7886 | 126.7 |
| Cd | 8.9938 | 137.9 |
| Pb | 7.4167 | 167.2 |
| Se | 9.7524 | 137 |
| Zn | 9.3942 | 132 |

Table 1 is meant primarily as an illustration for what would be needed in terms of UV wavelength(s) for ionization and subsequent oxide formation of the above-listed elements. Given different efficiencies of fabricated systems, final values may have to be adjusted per empirical data during burn in. Second ionization energies of each element are higher than that same element's first ionization energy.

The process is carried out at temperatures of from about 20° C. (68° F.) to 300° C. (572° F.).

Suitable other oxidizing sources or agents include, but are not limited to, water ($H_2O$), nitrogen oxides ($NO_x$), carbon dioxide ($CO_2$), and sulfur oxides ($SO_x$). These gases are found in effluent gas streams.

Other mercury oxidation products can include, but are not limited to mercury (I) (mercurous) sulfate ($Hg_2SO_4$), mercury (II) (mercuric) sulfate ($HgSO_4$), mercury (II) (mercuric) chloride ($HgCl_2$), mercury (I) (mercurous) chloride ($Hg_2Cl_2$), and mercury (II) (mercuric) chloride trihydrate ($HgCl_2 \cdot 3H_2O$). The oxidation products of the other elements given in Table 1 would be similar with similar chemical formulas.

When the oxidizing gas is oxygen ($O_2$), its concentration can be from about 3 mole percent (mol %) to 95 mol percent. The optimal value for this reaction parameter is approximately 20 to 21 mol percent, the oxygen content of air.

A UV lamp is used as the UV light source 20. For the wavelength of 253.7 nm, the lamp intensity can range from of about 1.0 mW/cm² to 10,000 mW/cm², preferably 5 to 500 mW/cm², and most preferably 10 mW/cm². The minimal light intensity is that required to cause the reaction in Equation 1 to go to completion with any of the oxidizing agents listed supra as a reactant and with photodeposited HgO as the end product.

The effluent gas stream flow rate ranges from about 20 milliliters per min (mL/min) to 10,000 mL/min (10 Liters(L)/min) with a preferred value being 10 L/min. The detection/reaction time can range from of about 1 second (sec) to 15 minutes.

The run time for the particular emission monitoring will depend upon the mass sensitivity of the piezoelectric sensor.

The inventors have also found that the sensor's substrate's are regenerable by heating the substrates to temperatures in excess of 510° C. (950° F.) to convert the heavy metal oxides back into gaseous elemental metals and thus renew the substrate's surfaces. The metalloid oxides are also removable from the substrate's surface's via heating as described. Arsenic trioxide ($As_2O_3$) and selenium dioxide ($SeO_2$) sublime at 193° C. and 340° C. to 350° C., respectively. Selenium trioxide ($SeO_3$) decomposes at 180° C.

The gas residence times (irradiated reactor volume divided by the gas flow rate) for all runs in Examples 1, 2 and Tables 2 and 3 infra is approximately 2 seconds (sec). This figure is near the residence time of flue gas found in a power generation facility's ductwork before the particulate collection device (PCD).

For the data in Tables 2 and 3 infra, a KCl solution captured oxidized Hg, allowing elemental Hg to pass through for adsorption onto a gold trap. A NaOH solution captured acid gases, e.g., $SO_x$, to prevent poisoning of the trap. Mercury collected on the gold trap was released by heating to 600° C. The mass of released mercury was then measured using a Buck Scientific Cold Vapor Atomic Absorption (CVAA) spectrometer (East Norwalk, Conn.). Sample collection time varied from 3 minutes to 5 minutes, depending on expected Hg concentration, with a sample flow of 500 milliliters (mL)/min through the trap.

Example 1

A model effluent gas stream was examined using a quartz photoreactor previously described and referenced. The reactor was a 10 inch long by ¼ inch outer diameter (⅙-in-inner-diameter) quartz tube with a 6-watt UV lamp. The lamp was at a fixed distance of 1.75 centimeters (cm) from the quartz photoreactor. At that distance, the intensity of 253.7 nm light is 1.4±0.07 milliWatts per square centimeter (mW/cm²).

Three 60 milliliters per minute (mL/min) slipstreams of particulate-free simulated flue gas were fed through a laboratory scale reactor at three different constant temperatures of 80° F. (27° C.), 280° F. (138° C.), and 350° F. (177° C.).

The simulated flue gas used in these three experiments contained carbon dioxide ($CO_2$) (16 mole (mol) percent (%)), oxygen ($O_2$) (5 mol %), sulfur dioxide ($SO_2$) (2000 parts per million (ppm)), 300 parts per billion (ppb) Hg, and nitrogen ($N_2$) (balance of about 79 mol %).

Once at thermal equilibrium, simulated fuel gases flow through a quartz photoreactor that is irradiated with 253.7 nanometers light for 350 minutes, which is the time length of the experiment. The gas residence time (irradiated reactor volume divided by the gas flow rate) is approximately two seconds.

The results are given in Table 2 infra.

Example 2

This series of experiments had substantially the same conditions as the conditions given in Example 1 supra except that there were eight experimental trials, at 280° F. (138° C.), and the simulated flue gas used in this experiment also contained 500 ppm of nitric oxide (NO). The result is given in Table 2 infra.

TABLE 2

Photochemical Removal[1,2]

| Example | Temp (° F./° C.) | Mean Hg Capture (%) |
|---|---|---|
| 1 | 350/177[5] | 2.3 ± 2.0[3] |
| 1 | 280/138[5] | 71.6 ± 30.1 |
| 1 | 80/26 | 67.8 ± 28.8 |
| 2 | 280/138[5] | 26.8 ± 11.7[4] |

[1.] These data are for simulated flue gases containing 5 mol percent oxygen as opposed to the 21 mol percent oxygen (i.e. found in air) used in Table 3, infra.
[2.] The mercury is removed as mercuric oxide (HgO)/mercurous sulfate ($Hg_2SO_4$).
[3.] Temperatures above 300° C. cause thermal decomposition of ozone and reduce the extent of oxidation of elemental mercury.
[4.] Nitric oxide (NO) reduces the removal of Hg, possibly by consuming ozone.
[5.] The temperatures of 280° F./138° C. and 350° F./177° C. are typical temperatures found near a particulate collection device (PCD) in a coal-fired power plant.

1. These data are for simulated flue gases containing 5 mol percent oxygen as opposed to the 21 mol percent oxygen (i.e. found in air) used in Table 3, infra.
2. The mercury is removed as mercuric oxide (HgO)/mercurous sulfate ($Hg_2SO_4$).
3. Temperatures above 300° C. cause thermal decomposition of ozone and reduce the extent of oxidation of elemental mercury.
4. Nitric oxide (NO) reduces the removal of Hg, possibly by consuming ozone.
5. The temperatures of 280° F./138° C. and 350° F./177° C. are typical temperatures found near a particulate collection device (PCD) in a coal-fired power plant.

These data are for a gaseous slip stream oxygen content of 5 mol percent as opposed to the 21 mol percent of air as used in Table 3 infra. The temperatures demonstrate that an optimal temperature range for the instant invention is from of about 80° F. (26° C.) to 280° F. (128° C.).

Table 3 demonstrates the effect of higher concentrations of oxygen upon Hg removal as $HgO/HgSO_4$ during the photochemical step (that step designated as element 20 in FIG. 1.)

TABLE 3

Effect of $O_2$ Upon Hg Oxidation to $HgO/HgSO_4$ Film[1]

| Gas | Time (Hrs) | Removal HgO Film (%) |
|---|---|---|
| Air[2] | 6 | 100 |
| Air | 21 | 100 |
| 4% $O_2$ | 28 | 83 |

[1.] The operating temperature was 26° C. (80° F.).
[2.] Air has the preferred oxygen concentration of 20 to 21 mol percent.

1. The operating temperature was 26° C. (80° F.).
2. Air has the preferred oxygen concentration of 20 to 21 mol percent.

The results in Table 3 show that the adding of oxygen to an effluent gas can aid the continuous emission monitoring of Hg and other heavy metals and metalloids by a more complete removal of the heavy metal/metalloid moiety as its oxide, with subsequent and immediate deposition and detection upon the substrate of a SAW sensor. This means that the method is very accurate, and reliable with reproducible results.

The method is energy efficient and uses only a small slipstream of effluent gas.

The method employs a dry system for the conversion of metals and metalloids.

The heavy metals/metalloids are converted into oxides and deposited upon substrates of SAW sensors.

The oxides are immediately detected and measured.

The SAW substrates are readily regenerable by heating to elevated temperatures.

The addition of oxygen or another oxidizing agent aids to ensure oxidation of heavy metal/metalloids.

While the invention has been described with reference to details of the illustrated embodiments, these details are not intended to limit the scope of the invention as defined in the appended claims.

The embodiment of the invention in which an exclusive property or privilege is claimed is defined as follows:

1. A method for the semi-continuous detection of heavy metals including mercury and metalloids in effluent streams, the method comprising:
    (a) contacting the effluent to an oxidizing fluid;
    (b) subjecting the effluent to a first radiation to oxidize a first group of metals and metalloids;
    (c) depositing the oxidized metals and metalloids onto a first piezoelectric oscillator having a first oscillating frequency; and
    (d) determining a second oscillating frequency of the oscillator.

2. The method as recited in claim 1 wherein the effluent stream is a gas.

3. The method as recited in claim 1 wherein the second oscillating frequency varies from the first oscillating frequency when as little as 1 part per trillion of metals and metalloids are entrained in the effluent stream.

4. The method as recited in claim 1 wherein the oxidizing fluid is oxygen gas having a concentration of from about 3 mole percent to 95 mol percent.

5. The method as recited in claim 1 wherein the radiation is UV light having energy ranging from about 1.0 $mW/cm^2$ to 10,000 $mW/cm^2$.

6. The method as recited in claim 1 wherein the radiation is UV light having energy ranging from about 5 to 500 $mW/cm^2$.

7. The method as recited in claim 1 wherein the radiation is UV light having energy of 10 $mW/cm^2$ and a wave length of 253.7 nm.

8. The method as recited in claim 1 wherein the effluent gas stream has a flow rate of from about 20 milliliters per min (mL/min) to 10,000 mL/min (10 Liters(L)/min).

9. The method as recited in claim 1 wherein the second frequency is detected from about 0.001 second to 15 minutes after deposition of the oxidized metals and metalloids.

10. The method as recited in claim 1 further comprising converting mercury in effluent streams to the elemental form prior to step a).

11. The method as recited in claim 1 further comprising the steps of
    d) subjecting the effluent to a second radiation to oxidize a second group of metals and metalloids;
    e) depositing the oxidized second group of metals and metalloids onto a second piezoelectric oscillator having a third oscillating frequency; and f) determining a fourth oscillating frequency of the oscillator.

12. The method as recited in claim 11 further comprising the steps of
   g) subjecting the effluent to a third radiation to oxidize a third group of metals and metalloids;
   h) depositing the oxidized third group of metals and metalloids onto a third piezoelectric oscillator having a fifth oscillating frequency; and
   i) determining a sixth oscillating frequency of the oscillator.

13. The method as recited in claim 12 wherein the effluent is subjected to the first radiation, then the second radiation, then the third radiation.

14. The method as recited in claim 12 wherein the effluent is simultaneously subjected to the first radiation, the second radiation and the third radiation.

15. The method as recited in claim 14 wherein the first, second and third oscillators are arranged in parallel.

16. The method as recited in claim 14 wherein the effluent simultaneously contacts all of the oscillators.

17. A device for extracting metals and metalloids from effluent streams, the device comprising:
   a) a means for contacting the stream with an oxidizing fluid to create a mixture;
   b) a first means for irradiating the metals and metalloids in the mixture to produce a first group of oxides of the metals and metalloids;
   c) a first piezoelectric oscillator oscillating at a first frequency, said oscillator adapted to receive the first group of oxides;
   d) a means for determining a change in frequency of the first oscillator.

18. The device as recited in claim 17 wherein the means for irradiating includes ultra violet light.

19. The device as recited in claim 17 further comprising
   e) a second means for irradiating the metals and metalloids to produce a second group of oxides of the metals and metalloids;
   f) a second piezoelectric oscillator oscillating at a second frequency, said oscillator adapted to receive the second group of oxides;
   g) a means for determining a change in frequency of the second oscillator.

20. The device as recited in claim 17 wherein the effluent simultaneously contacts the first irradiating means and the second irradiating means.

21. The device as recited in claim 17 wherein the first oscillator and the second oscillator are arranged in parallel so as to simultaneously receive the first and second group of oxides.

\* \* \* \* \*